United States Patent [19]

Guerriero

[11] 4,409,971

[45] Oct. 18, 1983

[54] CIRCULO-SEGMENTAL SPANNING AND HOLDING APPARATUS

[76] Inventor: Frederico D. Guerriero, 7029 W. Grand Ave., Chicago, Ill. 60635

[21] Appl. No.: 380,111

[22] Filed: May 20, 1982

[51] Int. Cl.³ .......... A61F 5/04

[52] U.S. Cl. .......... 128/84 C

[58] Field of Search .......... 128/75, 84 R, 84 A, 128/84 B, 84 C, 85, 327

[56] References Cited

U.S. PATENT DOCUMENTS

| | | | |
|---|---|---|---|
| 2,198,908 | 4/1940 | Ellis | 128/84 R |
| 2,319,400 | 5/1943 | Hartmann et al. | 128/84 R |
| 2,454,319 | 11/1948 | Henderson | 128/84 A |
| 3,889,664 | 6/1975 | Heuser et al. | 128/75 |

*Primary Examiner*—John D. Yasko

*Attorney, Agent, or Firm*—Robert M. Ward

[57] ABSTRACT

The present invention is directed to an orthopedic traction device comprising a plurality of pressure plates for disposition intermittently disposed in spaced array about a selected anatomical portion for effecting traction. The pressure plates are spanned by at least one pressure strap such that intervening areas of the anatomical portion are not placed under pressure to retain circulation downstream thereof. A pivotably adjustable traction securement means is attached to the pressure plate on either side of the anatomical portion to permit adjustment of the angle of traction, thereby to vary the longitudinal distribution of the inwardly directed pressure on the pressure plates for adjusting the direction of the traction.

The scope of use of the circulo-segmental spanning, traction and holding apparatus of the present invention is not confined to traction only, but may also be applied for other purposes including, inter alia, tortion, rotation, counterpull, or other anatomical movements.

13 Claims, 5 Drawing Figures

FIG. 3
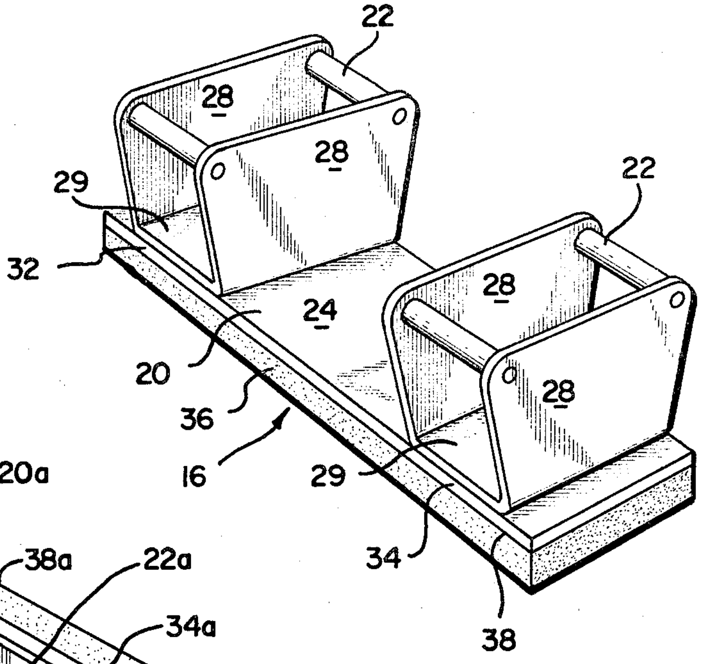
FIG. 4
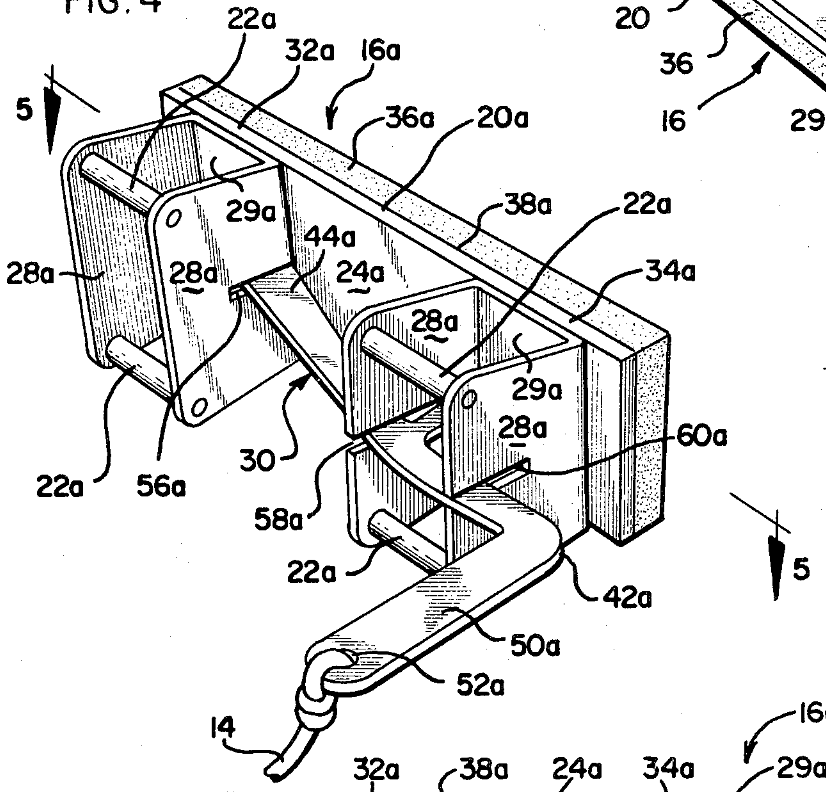
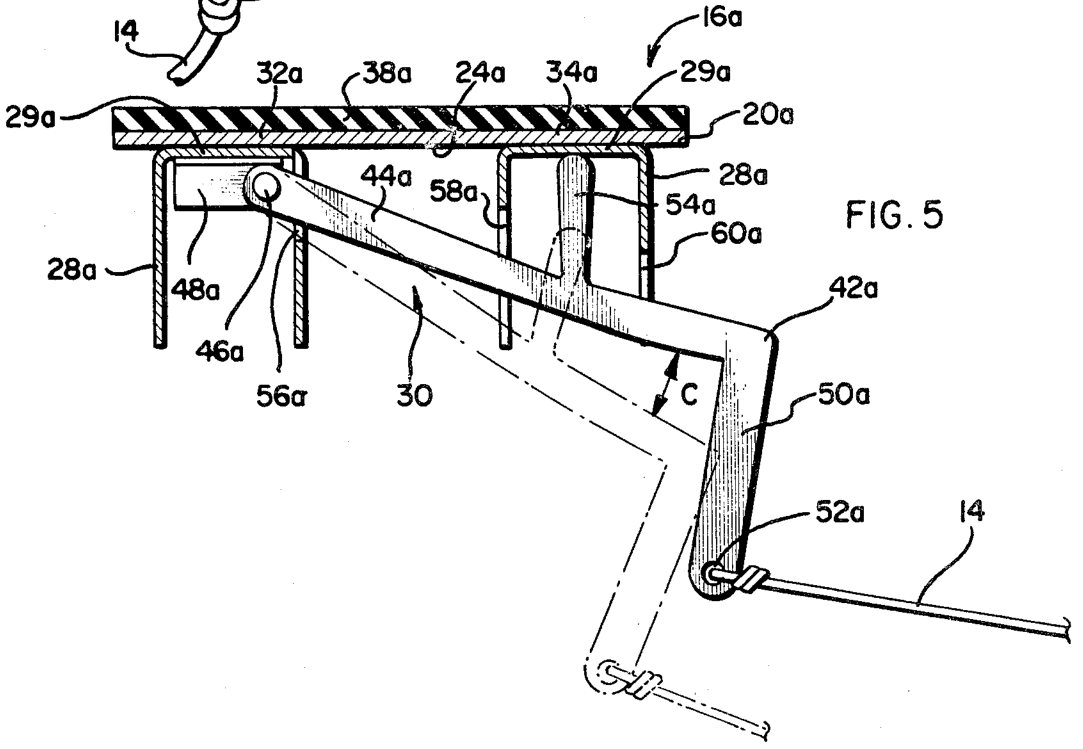
FIG. 5

CIRCULO-SEGMENTAL SPANNING AND HOLDING APPARATUS

BACKGROUND OF THE INVENTION

The present invention is directed generally to orthopedic devices, and more particularly to a circulo-segmental spanning and holding apparatus having means for adjusting the direction of the traction and means for adjusting the inwardly directed pressure of the apparatus against an anatomical portion.

In the prior art, certain anchorage means have been provided for the application of traction to an anatomical portion. In many instances, the prior art anchorage devices required the application of paste, tape or other adhesive substance against the skin with a circular bandage being applied around the anatomical portion. Such prior art structures have resulted in transmitting the force of the traction to the skin and to lower layers causing damage thereto.

In particular, such prior art devices have had, inter alia, the severe defect of effecting a sliding mechanism to lower anatomical layers including the application of longitudinally directed shear to the skin, which has had the further disadvantage of dispersing the force of traction to the anatomical layers, rather than to the skeletal structure requiring the traction. Additional disadvantages have been the causation of paid because of the shearing effect on the skin and because of the additional force necessary to effect the proper traction.

Also, many prior art devices which are secured by such adhesives have not been useable for any but limited time periods because of the degradation of the adhesive caused by constant shear and occasional movement of the patient. In many such instances, even slight movements of the patient, such as for example in adjusting position to prevent loss of circulation and bed sores or muscle cramps, have risked the danger of causing the adhesively secured traction devices to disengage. Should disengagement occur, the possibility of further damage and discomfort to the patient is increased.

Yet additionally, the lack of reuseability and the need of frequent replacement of adhesive based systems has in such prior art systems increased unnecessarily the cost of supplying traction to the patient.

Accordingly, in view of the shortcomings and disadvantages of prior art devices, it is an object of the present invention to alleviate materially these conditions and to provide an improved orthopedic traction apparatus.

SUMMARY OF THE INVENTION

The orthopedic traction apparatus of the present invention comprises a plurality of intermittently disposed pressure plates which are disposed circulo-segmentally about an anatomical portion. The pressure plates include pressure strap spanning means elevated above the base portion thereof, such that a pressure strap, which is preferably adjustable as to its inwardly directed pressure, may be secured about the plates to provide a uniform pressure at equally distributed radial positions around the anatomical portion to which the traction apparatus of the present invention is applied.

A traction securement means which is pivotably adjustable is attached to preferrably the distal end of the circulo-segmental plates for allowing a traction line to be angled, thereby to vary the longitudinal distribution of the inwardly directed pressure on the plates. Accordingly, greater or lesser pressure may be applied to the front or proximal portions of the plates, or to the rear or distal portions of the plates, as needed.

The novel structure of the circulo-segmental orthopedic traction apparatus of the present invention has resulted in an apparatus which is sturdy and reuseable, thereby lowering the cost of the traction to the patient. Additionally, with the orthopedic traction apparatus of the present invention, a much greater force of traction may be applied, with but minimal pain and discomfort to the patient. Morever, the sliding of the traction apparatus along the skin resulting in a shearing action on the skin and lower layers with damaging consequences and pain to the patient associated with prior art devices has been minimized. Additionally, the circulo-segmental spanning feature of the orthopedic traction apparatus of the present invention allows for intervening radial areas to be free of any pressure, which permits for greater circulation to downstream anatomical areas.

These and other advantages of the improved circulo-segmental spanning orthopedic traction apparatus of the present invention will become apparent to those skilled in the art in view of the following brief description of the drawing, detailed description of preferred embodiments, appended claims and accompanying drawing.

BRIEF DESCRIPTION OF THE DRAWINGS

FIG. 3 is a perspective view of one of the circulo-segmental plates as shown in FIGS. 1 and 2 of the kind for disposition above and below the leg, and comprising a resilient base portion disposed onto the underside of the base portion of the circulo-segmental pressure plate, and having upstandingly disposed from the upperside of the base portion respective interconnecting means for a plurality of roller-like pressure strap spanning means for receiving the pressure strap as shown in FIG. 2;

FIG. 4 is an accompanying circulo-segmental plate of the kind as shown in FIGS. 1 and 2 for abutting against the lateral and medial portions of the patient's leg and having pivotably adjustable traction securement means for allowing the traction line thereof to be adjustably angled, thereby to vary the longitudinal distribution of the inwardly directed pressure on the plates that is distributed to the patient's leg; and FIG. 5 is a longitudinal cross sectional view taken along line 5—5 of FIG. 4 and showing in particular the L-shaped angle member with pivot securement means for limiting the range of pivotability of the L-shaped angle member inwardly and for bearing against the inner surface of the plate member to direct pressure thereagainst.

DETAILED DESCRIPTION OF PREFERRED EMBODIMENTS

Figure 1:
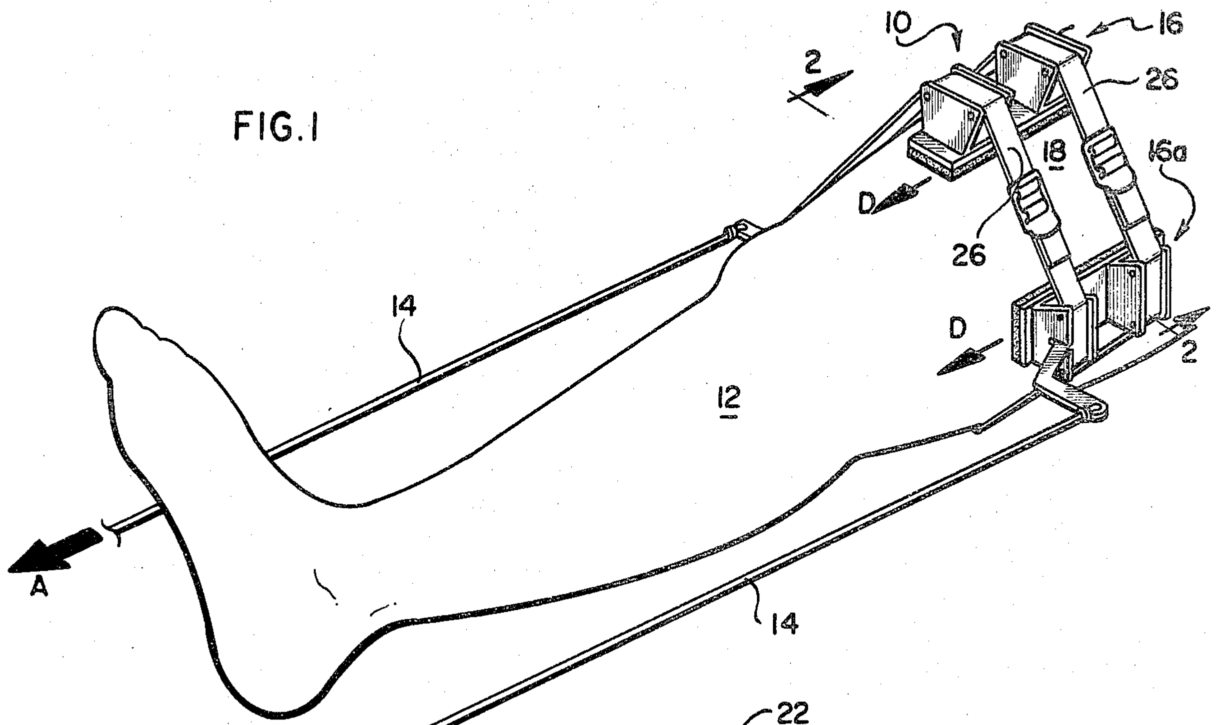
FIG. 1 is a perspective view showing the improved circulo-segmental orthopedic traction apparatus of the present invention applied to the leg of a patient undergoing traction in the direction as indicated by arrows A.

The orthopedic traction apparatus of the present invention is directed to various embodiments of devices for applying traction to a selected anatomical portion. The apparatus includes at least one, and preferably two, traction lines. A plurality of circulo-segmental plates are included for intermittent disposition in spaced radial array about the selected anatomical portion. The effect of such intermittent disposition is to retain circulation unimpeded in intervening areas between the pressure plates thereby to minmize circulatory problems downstream of the segmentally pressured anatomical portion against which the pressure plates of the orthopedic traction apparatus of the present invention are engaged. Each of the pressure plates comprises a base portion which is contoured to rest in substantially flat configuration against the anatomical portion. At least one pressure strap spanning means is disposed elevated from the base portion of the plate for pressure contact with the pressure strap means. Means are provided on and elevated above the upper surface of said pressure plate base portion for interconnecting the plate with the spanning means to retain the spanning means in spaced elevation from the said base portion.

At least one pressure strap is provided for disposition about the circulo-segmental plates. The pressure strap is affixed radially about the circulo-segmental plates and in firm contact with the strap spanning means for exerting an inward pressure thereon to hold the pressure plate sufficiently firmly against the anatomical portion. Thus, stable means for anchoring at least one traction line are disposed about and firmly secured to the anatomical portion.

Pivotably adjustable securement means are attached to at least one of the circulo-segmental plates for allowing the corresponding traction line to be adjustably angled. This adjustable angling feature of the circulo-segmental spanning traction apparatus of the present invention functions to vary the longitudinal distribution of the inwardly directed pressure on the pressure plates.

In preferred embodiments of the orthopedic traction apparatus of the present invention, the plates may preferably include a pair of pressure strap spanning means disposed substantially at each of the distal and proximal ends thereof. The pressure strap spanning means preferably includes at least one roller disposed longitudinally with respect to the base portion of the pressure plates, and thus longitudinally with respect to the selected anatomical portion, and transversely with respect to the pressure straps.

Other preferred embodiments of the orthopedic traction apparatus of the present invention may preferably include a pair of pressure straps urging both the proximal and distal ends of the base portion of the pressure plate inwardly and against the selected anatomical portion.

In preferred embodiments, the pressure plates also include a non-binding and resilient pad means secured to the inner surface of the base portion of the pressure plates. Such non-binding and resilient pad means serve to prevent longitudinally directed shearing action on the skin of the anatomical portion to which the pressure plates are applied, and also to prevent trauma to the inner layers of the anatomical portion caused by the inwardly directed pressure thereon.

In preferred embodiments, four of the pressure plates are spaced radially about the anatomical portion, such as for example a leg—one each at the top, bottom, and each side of the anatomical portion.

The pivotably adjustable traction means in preferred embodiments may preferably comprise a generally L-shaped angle member. The L-shaped angle member in preferred embodiments has a generally longitudinally disposed first portion for pivotably connecting preferably to the upper surface of the distal end of the pressure plate. A generally transversely disposed second portion is connected to the longitudinally disposed first portion at one end thereof and is connected to the traction line at the opposite end thereof. Such L-shaped members preferably include a pivot stop means disposed opposite the second or traction line connecting portion thereof for bearing against the upper surface of the base portion of the pressure plate to limit the range of inward pivotability thereof.

Also in preferred embodiments, the pressure strap spanning interconnecting means includes aperture means for permitting inward motion of the proximal end of the first portion of the L-shaped angle member toward the upper surface of the base portion of the pressure plate.

The pressure strap utilized in the orthopedic traction apparatus of the present invention preferably includes adjustable means for varying the inwardly directed pressure on the circulo-segmental pressure plates.

In preferred embodiments, the pressure strap includes securement means for holding the pressure strap at a selected and stable tension in its radial disposition about the pressure plate. The pressure strap securement means may comprise in some embodiments hook and loop tape fastening means, such as is sold under the trademark "Velcro". In alternative preferred embodiments, a cinch buckle of the well-known variety may be utilized.

Referring now to the drawing in which common reference numerals are utilized for common elements, FIG. 1 shows a preferred embodiment of the circulo-segmental spanning traction apparatus of the present invention generally designated at 10 applied to leg 12 of a patient for effecting traction in the direction of arrows A.

Figure 2:
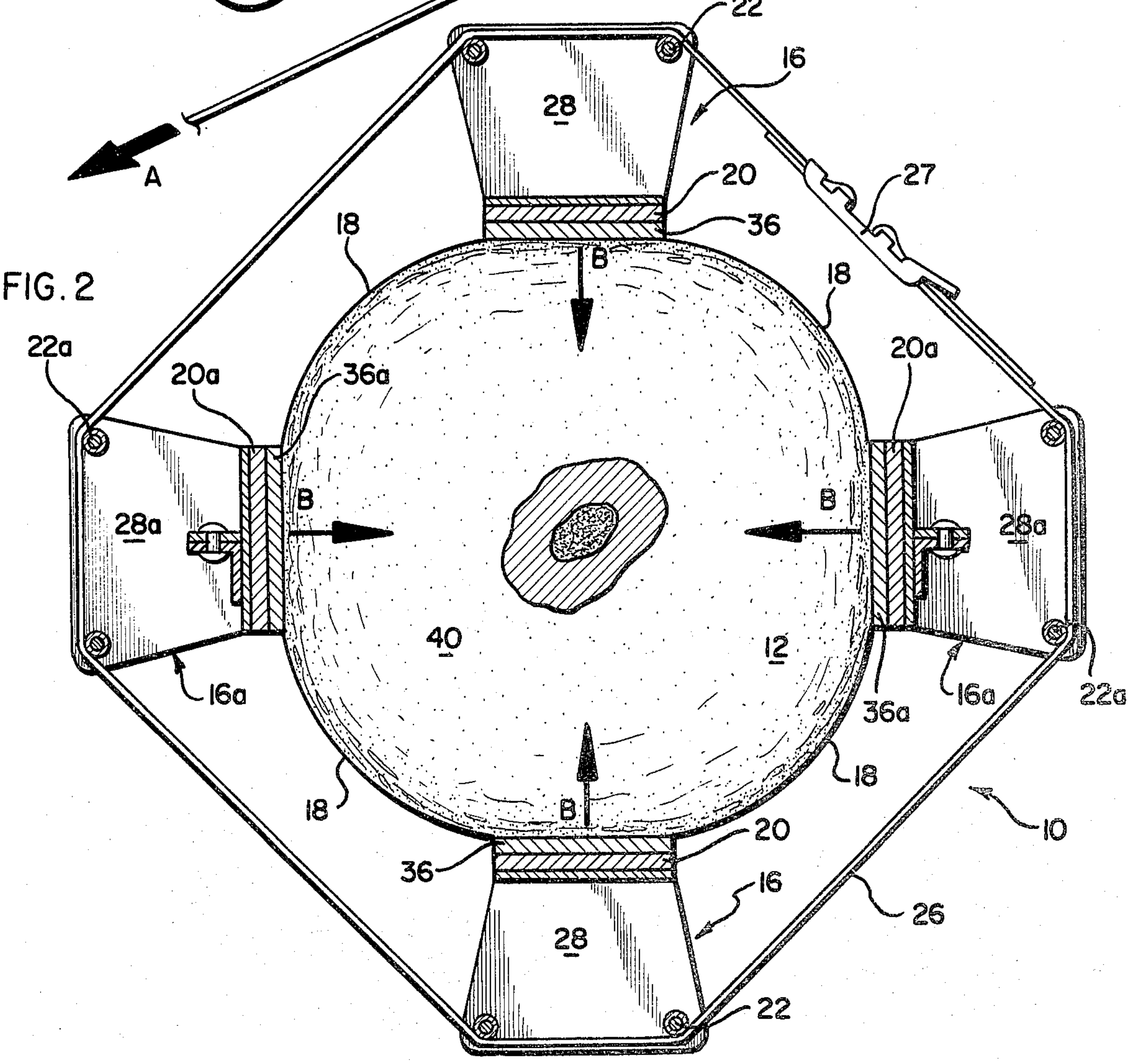
FIG. 2 is an enlarged transverse cross sectional view taken along lines 2—2 of FIG. 1 showing the adjustable pressure strap disposed about the circulo-segmental pressure plates in contact with the pressure strap spanning means thereof to exert an inwardly directed pressure thereon to the patient's leg in the direction of arrows B, thereby to hold the pressure plates firmly against the leg and to provide stable means for anchoring the traction lines.

Orthopedic traction apparatus 10 includes preferably two traction lines 14, 14. A plurality of circulo-segmental plates of two different kinds generally 16 and **16*a* are included for intermittent disposition in spaced radial array about leg 12, as shown in FIGS. 1 and 2, although other anatomical portions may be selected for application thereto. In such disposition as shown in FIG. 1, the circulation is unimpeded in intervening areas 18 also shown in FIG. 2 between pressure plates 16, 16*a*, thereby to minimize circulatory problems downstream in leg 12. As is described hereinbelow in greater detail there are two separate kinds of pressure plates 16, 16*a* are utilized in orthopedic traction apparatus 10, and common elements utilize common reference numerals with the further designation a to indicate the elements of the pressure plate 16*a* having pivotably adjustable securement means associated therewith Each of the pressure plates 16, 16*a* comprises a base portion 20, 20*a* which is contoured to rest in substantially flat configuration against leg 12. Pressure strap spanning means shown in the form of rollers 22, 22*a* are disposed elevated from upper surface 24, 24*a* plate for pressure contact with pressure strap means 26. Pressure strap 26 includes a buckle 27 as shown in FIGS. 1 and 2** although other securement means may be utilized as described, supra. Upstanding wing plates 28, 28a serve as means on pressure plates 16, 16a for interconnecting the plate with the spanning roller means 22, 22a to retain spanning roller means 22, 22a in spaced elevation from base portion 20,20a. Upstanding wing plates 28, 28a may preferably be form as a one-piece channel having a channel bottom portion 29, 29a, as shown in FIGS. 3, 4 and 5.

As shown in FIG. 1 in particular, two pressure straps 26, 26 are provided for disposition about circulo-segmental pressure plates 16, 16a. Pressure straps 26, 26 are affixed radially about circulo-segmental plates 16, 16a and in firm contact with strap spanning roller means 22, 22a for exerting an inward pressure thereon, as shown at Arrows B in FIG. 2, to hold pressure plates 16, 16a sufficiently firmly against leg 12. Thus, stable means for anchoring traction lines 14, 14 are disposed about leg 12.

As shown most particularly in FIGS. 4 and 5, pivotably adjustable securement means generally 30a are attached to circulo-segmental plates 16a for allowing the corresponding traction line 14 to be adjustably angled and pivoted as shown at arrow C in FIG. 5. This adjustable angling feature of circulo-segmental spanning traction apparatus 10 functions to vary the longitudinal distribution of the inwardly directed pressure on plates 16a.

As shown in The Figs. hereof, plates 16, 16a include a pair of pressure strap spanning roller means 22, 22 and 22a, 22a disposed substantially at each of distal end 32, 32a and proximal end 34, 34a thereof. Rollers 22, 22a are disposed longitudinally with respect to base portion 24, 24a of pressure plates 16, 16a and thus longitudinally with respect to leg 12 and transversely with respect to pressure straps 26, 26.

Pressure plates 16, 16a have a non-binding and resilient pad means 36, 36a secured to the inner surface 38, 38a of base portion 20, 20a the pressure plates 16, 16a. Pad means 36, 36a serve to prevent longitudinally directed shearing action on the skin of leg 12, as should otherwise occurs in the direction of Arrow D of FIG. 1, and also to prevent trauma to the inner layers 40 of leg 12, as shown in FIG. 2 in particular.

Pressure plates 16, 16a are spaced radially about leg 12, at the top, bottom and each side of leg 12. As shown in FIGS. 4 and 5, pivotably adjustable traction means 30 preferably comprise a generally L-shaped angle member 42a. L-shaped angle member 42a inlcudes generally longitudinally disposed first portion 44a which is pivotably connected at pin 46a to pivot attachment bracket 48a as shown in FIG. 5. Pivot bracket 48a is in turn fixed connected to upper surface 24a of plate 16a. Generally transversely disposed second portion 50a is connected to longitudinally disposed first poriton 44a at one end thereof and is connected to traction line 14 at the opposite end thereof at traction line aperture 52a. L-shaped member 42a preferably includes a pivot stop member 54a disposed opposite second connecting portion 50a for bearing against base portion 20a of pressure plate 16a to limit the range of inward pivotability thereof as shown in FIG. 5. Additionally, wing plates 28a include slits 56a, 58a and 60a for permitting pivotable inward motion as shown at Arrow C of FIG. 5 of the proximal end of first portion 44a of L-shaped angle member 42a toward upper surface 24a of base portion 20a of pressure plate 16a.

The circulo-segmental pressure plates including the base portion, pressure strap spanning means in the form of preferred rollers, and means for interconnecting the base portion of the plate and the rollers, as well as the L-shaped angle member, are preferrably formed from a light metal, such as aluminum, although plastics may be used in other preferred embodiments. The non-binding and resilient pad means secured to the inner surface of the pressure plate base portion may comprise any of a variety of rubbers or polymeric or copolymeric substances, either with or without gaseous bubbles entrained therein, or other substances dispersed therein. The pressure strap is preferably formed of nylon, and the securement means thereof may be formed of metal, plastic, or hook and loop tape.

Although the invention has been described in terms of a preferred construction of a circulo-segmental spanning traction apparatus, it will be apparent to those skilled in the art that many alterations and modifications may be made without departing from the invention. Accordingly, all such alterations and modifications are intended to be considered as within the spirit and scope of the invention as defined by the appended claims.

What is claimed is:

1. An orthopedic traction apparatus for application to a selected anatomical portion for applying traction, said apparatus comprising:

at least one traction line;

a plurality of circulo-segmental pressure plates intermittantly disposed in spaced radial array about the selected anatomical poriton whereby circulation is unimpeded in intervening areas between said plates, each said plate comprising a base portion contoured to rest in substantially flat configuration against the anatomical portion, at least one pressure strap spanning means disposed elevated from said plate for inwardly directed pressure contact with a pressure strap, and means interconnecting said plate and said spanning means for retaining said spanning means in spaced elevation from said pressure plate means base portion;

at least one pressure strap for disposition radially about said circulo-segmental plates and in firm contact with said strap spanning means for exerting an inward pressure thereon for holding said plates sufficiently firmly against the anatomical portion to provide stable means for anchoring said at least one traction line; and pivotably adjustable traction securement means attached to at least one of said circulo-segmental plates for allowing said at least one traction line to be adjustably angled for varying the longitudinal distribution of the inwardly directed pressure on said plates.

2. The orthopedic traction apparatus of claim 1 wherein said plates include a pair of pressure strap spanning means disposed substantially at each of the distal and proximal ends hereof.

3. The orthopedic traction apparatus of claim 2 comprising a pair of pressure straps for urging both the proximal and distal ends of said base portion of said pressure plate inwardly against the selected anatomical portion.

4. The orthopedic traction apparatus of claim 1 wherein said pressure strap spanning means comprise at least one roller disposed longitudinally with respect to said base portion of said pressure plates and the selected anatomical portion and transversely with respect to said pressure strap.

5. The orthopedic traction apparatus of claim 1 wherein said pressure plates further include non-binding and resilient pad means secured to the inner surface of said portion thereof for prevention of longitudinally directed shearing action on the skin of the anatomical portion to which said pressure plates are applied and for prevention of trauma to the inner layers of the anatomical portion from the inwardly directed pressure thereon.

6. The orthopedic traction apparatus of claim 1 comprising four said pressure plates for spacing at the top, bottom and both sides of the selected anatomical portion.

7. The orthopedic traction apparatus of claim 1 wherein said pivotably adjustable traction means comprises:

a generally L-shaped angle member having a generally longitudinally disposed first portion pivotably attached at the distal end thereof to said base portion, and a generally transversely disposed second portion connected to said longitudinally disposed first portion at and having oppositely disposed on said record portion means for connection to a said traction line.

8. The orthopedic traction apparatus of claim 7 wherein said L-shaped member includes pivot stop means disposed opposite said second, traction line connecting portion for bearing against said base portion of said pressure plate to limit the inward range of pivotability thereof.

9. The orthopedic traction apparatus of claim 7 wherein said plate and pressure strap interconnecting means includes aperture means for permitting inward motion of the proximal end of said first portion of said L-shaped angle member toward the outer surface of said base portion.

10. The orthopedic traction apparatus of claim 1 wherein said pressure strap includes adjustable means for varying the inwardly directed pressure on said circulo-segmental plates.

11. The orthopedic traction apparatus of claim 1 wherein said pressure strap includes securement means for holding at selected and stable tension said pressure strap in radical disposition about said pressure plates.

12. The orthopedic traction apparatus of claim 11 wherein said pressure strap securement means comprises hook and loop tape fastening means.

13. The orthopedic traction apparatus of claim 11 wherein said pressure strap securement means comprises a cinch buckle.

* * * * *